(12) United States Patent
Arimoto et al.

(10) Patent No.: US 10,130,094 B2
(45) Date of Patent: Nov. 20, 2018

(54) PESTICIDAL/OVICIDAL COMPOSITION AND PESTICIDAL/OVICIDAL METHOD

(71) Applicant: RIKEN, Wako-shi, Saitama (JP)

(72) Inventors: Yutaka Arimoto, Wako (JP); Kenichi Tanaka, Wako (JP)

(73) Assignee: RIKEN, Wako-Shi, Saitama (JP)

( * ) Notice: Subject to any disclaimer, the term of this patent is extended or adjusted under 35 U.S.C. 154(b) by 0 days.

(21) Appl. No.: 14/706,430

(22) Filed: May 7, 2015

(65) Prior Publication Data

US 2015/0230459 A1 Aug. 20, 2015

Related U.S. Application Data

(63) Continuation of application No. 12/296,358, filed as application No. PCT/JP2007/057848 on Apr. 9, 2007.

(30) Foreign Application Priority Data

Apr. 7, 2006 (JP) ................. 2006-106727

(51) Int. Cl.
*A01N 37/06* (2006.01)

(52) U.S. Cl.
CPC .................... *A01N 37/06* (2013.01)

(58) Field of Classification Search
CPC .................................................. A01N 37/06
See application file for complete search history.

(56) References Cited

U.S. PATENT DOCUMENTS

| 6,294,578 B1 | 9/2001 | Arimoto | |
| 2001/0055628 A1* | 12/2001 | Hsu | A01N 65/00 424/736 |
| 2006/0165748 A1* | 7/2006 | Arimoto | A01N 37/02 424/405 |

FOREIGN PATENT DOCUMENTS

| JP | 53-047532 A | 4/1978 | |
| JP | 56-092207 A | 7/1981 | |
| JP | 56-138105 A | 10/1981 | |
| JP | 56-140911 A | 11/1981 | |
| JP | 10-251104 A | 9/1998 | |
| JP | WO 2005004602 A1 * | 1/2005 | ............ A01N 37/02 |
| JP | 2005-029489 A | 2/2005 | |
| WO | WO 91/18508 | 12/1991 | |
| WO | WO 2005/004602 | 1/2005 | |
| WO | WO 2005115144 A1 * | 12/2005 | ............ A01N 57/12 |
| WO | WO 2006/028170 | 3/2006 | |

OTHER PUBLICATIONS

Fuller et al.; "High-Oleic Safflower Oil. Stability and Chemical Modification"; 1967; Journal of the American Oil Chemist's Society; 44: 264-266.*

Arnold et al.; "The Fatty Acid Composition of Stages of Solvent Extraction"; 1961; Journal of the American Oil Chemists Society; 38(2): 87-88.*

Form PCT/ISA/210 (International Search Report) dated May 15, 2007.

Non-English version of Form PCT/ISA/237 (Written Opinion the International Searching Authority) dated May 15, 2007.

Supplementary European Search Report dated Feb. 29, 2012, issued in related European Patent Application 07741284.9.

Fuller et al. "*High-Oleic Safflower Oil. Stability and Chemical Modification*" 44 Journal of the American Oil Chemist's Society 264-266 (1967.

* cited by examiner

*Primary Examiner* — Timothy P Thomas

(74) *Attorney, Agent, or Firm* — Buchanan, Ingersoll & Rooney PC

(57) ABSTRACT

A pesticidal/ovicidal composition comprising: (a) 50-99.9 parts by mass of a triglyceride containing not less than 50% of oleic acid as a fatty acid component; (b) 0.1-20 parts by mass of a nonionic surface active agent; and (c) 0-30 parts by mass of a glycerin derivative. The composition according to the invention has not only a pesticidal activity but also an ovicidal activity on crop pests, and provides a safe and high pesticidal/ovicidal effect.

4 Claims, 2 Drawing Sheets

PESTICIDAL/OVICIDAL COMPOSITION AND PESTICIDAL/OVICIDAL METHOD

CROSS-REFERENCE TO RELATED APPLICATIONS

This application is a Continuation Application of U.S. patent application Ser. No. 12/296,358, filed on Oct. 7, 2008, which is a U.S. National Stage Application pursuant to 35 U.S.C. § 371 of International Patent Application PCT/JP2007/057848, filed on Apr. 9, 2007, and published as WO 2007/117001 on Oct. 18, 2007, which claims priority to Japan Patent Application 2006-106727, filed on Apr. 7, 2006.

TECHNICAL FIELD

The present invention relates to a pesticidal/ovicidal composition and a pesticidal/ovicidal method.

BACKGROUND ART

Various agents have been known as a fungicide and a triglyceride-based pesticidal composition against crop pests such as mites and aphids. For example, Patent Document 1 discloses a fungicidal composition comprising a phospholipid and an edible oil. Patent Documents 2 to 4 disclose a miticide comprising animal and vegetable oils and a surfactant. These Documents, however, do not disclose that the above compositions work on mite eggs.

Patent Document 5 discloses a triglyceride composed of unsaturated fatty acid, which shows high pesticidal and ovicidal effects by combining a coconut oil, a palm kernel oil, triglyceride composed of $C_{12}$ and $C_{14}$ fatty acids (mixing ratio: from 4:1 to 1:4), triglyceride composed of $C_{12}$ and $C_{18-1}$ fatty acids (mixing ratio: from 4:1 to 1:4), triglyceride composed of $C_{12}$, $C_{14}$ and $C_{18-1}$ fatty acids (mixing ratio: 1-4:1-4:1-4), triglyceride composed of $C_{10}$ and $C_{18-1}$ fatty acids (mixing ratio: from 4:1 to 1:4), trioleate, and DO-100 (diglycerol oleate) or DL-100 (diglycerol laurate) with a specific adjuvant. However, since glycerides other than the coconut oil and the palm kernel oil are synthetically produced, they require high production costs and are of little practical use.

Accordingly, in recent years, there is a demand for an agent, which is amenable to various applications, has no risk of drug resistance induction, and is safe for crops and natural environment-friendly.

Patent Document 1: JP-A-53-47532
Patent Document 2: JP-A-56-92207
Patent Document 3: JP-A-56-138105
Patent Document 4: JP-A-56-140911
Patent Document 5: JP-A-2005-29489

DISCLOSURE OF THE INVENTION

Problems to be Solved by the Invention

Accordingly, an object of the invention is to provide a pesticidal/ovicidal composition which has not only a pesticidal effect but also an ovicidal effect on crop pests.

Another object of the invention is to provide a pesticidal/ovicidal method against crop pests.

MEANS TO SOLVE THE PROBLEMS

Figure 1:
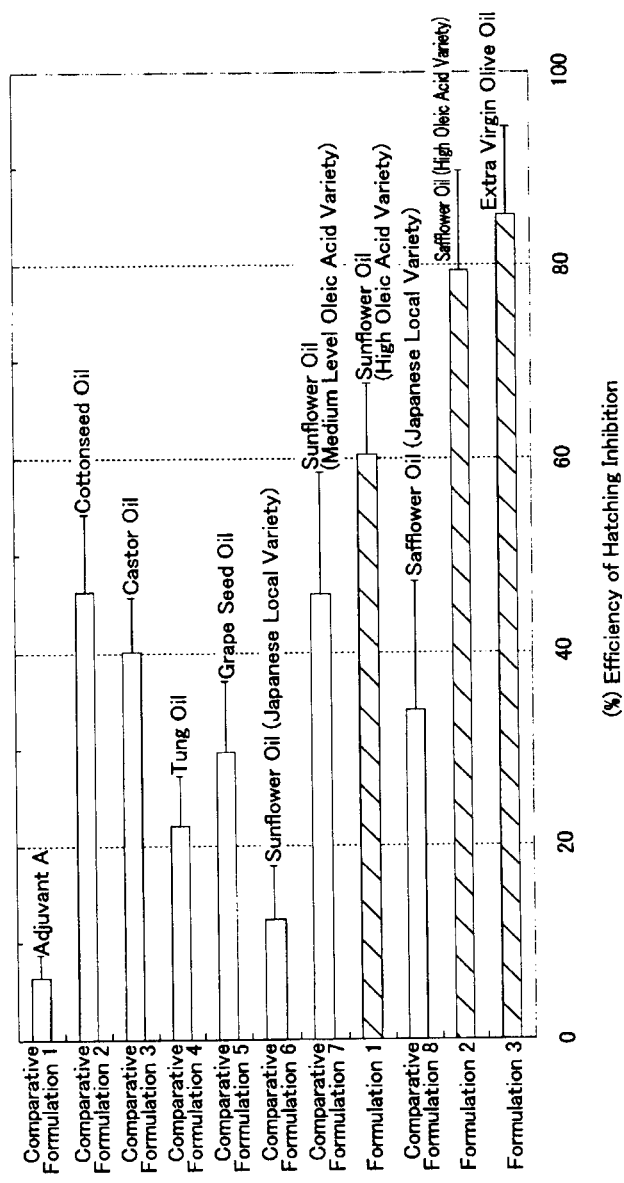
FIG. 1 sets forth the results of Experimental Example 1: Effect on *Tetranychus urticae* Koch eggs, wherein the percent efficiency of hatching inhibition of Formulations 1-3 and comparative Formulations 1-8 was examined.

The present invention has been completed based on a finding that fats and oils having a particular fatty acid composition display excellent pesticidal/ovicidal effects on imagines, larvae and eggs of crop pests. The invention provides pesticidal/ovicidal compositions and pesticidal/ovicidal methods as described below.

1. A pesticidal/ovicidal composition comprising:
(a) 50-99.9 parts by mass of a triglyceride containing not less than 50% of oleic acid as a fatty acid component;
(b) 0.1-20 parts by mass of a nonionic surface active agent; and
(c) 0-30 parts by mass of a glycerin derivative.

2. The pesticidal/ovicidal composition according to above item 1, wherein said nonionic surface active agent is at least one selected from the group consisting of fatty acid esters and amino acid derivatives.

3. The pesticidal/ovicidal composition according to above item 2, wherein said nonionic surface active agent is a fatty acid ester, wherein said fatty acid ester is at least one selected from the group consisting of polyoxyethylene fatty acid esters, sorbitan fatty acid esters, polyoxyethylene sorbitan fatty acid esters and polyoxyethylene glyceryl ether fatty acid esters.

4. The pesticidal/ovicidal composition according to above item 3, wherein said fatty acid ester is a polyoxyethylene fatty acid ester, wherein said polyoxyethylene fatty acid ester is at least one selected from the group consisting of polyoxyethylene castor oil, and polyoxyethylene hydrogenated castor oil.

5. The pesticidal/ovicidal composition according to any one of above items 1 to 4, further comprising:
(d) a lower alcohol in an amount not more than 10 parts by mass; and/or
(e) a vegetable oil in an amount not more than 39 parts by mass,
relative to 100 parts by mass of the total amount of the components (a), (b) and (c).

6. The pesticidal/ovicidal composition according to any one of above items 1 to 5, which is diluted by 100-fold to 1000-fold with water.

7. A pesticidal/ovicidal method which comprises the step of spraying to crops the pesticidal/ovicidal composition according to any one of above items 1 to 6, in such an amount that the total amount of the components (a), (b) and (c) is in the range between 0.2 kg/10a and 8 kg/10a.

8. The pesticidal/ovicidal method according to above item 7 which comprises the step of spraying to crops the pesticidal/ovicidal composition, in such an amount that the total amount of the components (a), (b) and (c) is in the range between 0.5 kg/10a and 3 kg/10a.

Effects of the Invention

Since the pesticidal/ovicidal composition according to the invention employs triglyceride, which is used in food, as a main ingredient, it has no stress on human bodies and natural environments and no risk of drug resistance induction, and shows pesticidal and ovicidal effects even on crop pests which already have acquired resistances to other drugs. In addition, the composition according to the invention displays sufficient pesticidal and ovicidal effects even at lower concentrations.

BEST MODES FOR CARRYING OUT THE INVENTION

The triglyceride component (a) used for the composition of the invention contains oleic acid as a constituent fatty acid in an amount not less than 50%, preferably, not less than 55%, and more preferably, not less than 60% by mass. Examples of such triglyceride include olive oil (containing oleic acid in an amount of 60-80% by mass), extra virgin olive oil (60-80% by mass), camellia oil (about 85% by mass), almond oil (60-70% by mass), avocado oil (64-94% by mass), tea seed oil (about 88% by mass), safflower oil (high oleic acid variety) (70-80% by mass), sunflower oil (high oleic acid variety) (75-80% by mass), and oils from other high oleic acid plants. Among these, sunflower oil (high oleic acid variety), safflower oil (high oleic acid variety) and extra virgin olive oil are preferred.

The composition according to the invention contains component (a) in an amount of 50-99.9 parts by mass, preferably, 70-99.9 parts by mass, and more preferably, 80-99.9 parts by mass, relative to 100 parts by mass of the total amount of components (a), (b) and (c). Triglyceride content of 50-99.9 parts by mass is preferred for the composition of the invention, because triglyceride content in such range tends to exert pesticidal/ovicidal effect.

For the composition of the invention, an adjuvant containing component (b) or components (b) and (c) is used.

Adjuvant component (b) is a nonionic surface active agent, and preferably at least one selected from the group consisting of fatty acid esters and amino acid derivatives.

Examples of the fatty acid esters include polyoxyethylene fatty acid esters, sorbitan fatty acid esters, polyoxyethylene sorbitan fatty acid esters and polyoxyethylene glyceryl ether fatty acid esters.

Examples of the polyoxyethylene fatty acid esters include polyoxyethylene castor oil and polyoxyethylene hydrogenated castor oil. Polyoxyethylene castor oil is most preferable.

The mole number of polyoxyethylene groups added is preferably between 5-80 moles, more preferably between 10-60 moles, and most preferably between 20-50 moles.

The amino acid derivatives are preferably pyroglutamic acid esters, and more preferably, N-acyl glutamic acid esters.

The pesticidal/ovicidal composition of the invention contains component (b) in an amount of 0.1-20 parts by mass, preferably, 0.1-10 parts by mass, and more preferably, 0.5-5 parts by mass, relative to 100 parts by mass of the total amount of the components (a), (b) and (c).

Preferably, the pesticidal/ovicidal composition of the invention further includes a glycerin derivative as adjuvant component (c). Examples of the glycerin derivative for component (c) include monoglycerol fatty acid esters and polyglycerol fatty acid esters. More specifically, glycerol monoalkyl fatty acid esters, glycerol dialkyl fatty acid esters, polyglycerol monoalkyl fatty acid esters and polyglycerol polyalkyl fatty acid esters are included. Among these, polyglycerol fatty acid esters are preferred, and diglycerol fatty acid esters are more preferred. Preferably, constituent fatty acids for such esters are $C_{12}$-$C_{18}$ fatty acids, such as oleic acid and lauric acid.

Specific examples include diglycerol oleate (DO-100), diglycerol laurate (DL-100), tetraglycerol oleate (J-4581), hexaglycerol laurate (J-6021), decaglycerol oleate (J-0381), polyglycerol oleate (AG-7520) and the like.

The pesticidal/ovicidal composition of the invention may contain component (c) in an amount of 0-30 parts by mass, preferably, 0.5-20 parts by mass, and more preferably, 1.0-10 parts by mass, relative to 100 parts by mass of the total amount of components (a), (b) and (c).

The pesticidal/ovicidal composition of the invention may optionally include a lower alcohol as component (d). Examples of such a lower alcohol include a $C_1$-$C_4$ aliphatic alcohol, such as methanol, ethanol, 1-propanol, 2-propanol, 1-butanol, 2-butanol, isobutanol. Among these, ethanol, 1-propanol and 2-propanol are preferable, and 1-propanol and 2-propanol are more preferable.

The pesticidal/ovicidal composition of the invention may contain optional component (d) in an amount not more than 10 parts by mass, preferably, not more than 5 parts by mass, and more preferably, not more than 3 parts by mass, relative to 100 parts by mass of the total amount of components (a), (b) and (c). Use of lower alcohol as component (d) allows components (a), (b) and (c) to be mixed more uniformly, and increases their dispersibility in water. In order to achieve this, it is preferable to use the lower alcohol in an amount not less than 0.1 part by mass.

The pesticidal/ovicidal composition of the invention may optionally include, as component (e), a vegetable oil other than component (a). Examples of such vegetable oil include sesame oil, safflower oil, soybean oil, corn oil, sunflower oil and cottonseed oil. Among these, safflower oil, soybean oil, corn oil, sunflower oil and cottonseed oil are preferable, and soybean oil and cottonseed oil are more preferable.

The pesticidal/ovicidal composition of the invention may contain the optional component (e) in an amount not more than 39 parts by mass, preferably, not more than 20 parts by mass, and more preferably, not more than 15 parts by mass, relative to 100 parts by mass of the total amount of components (a), (b) and (c). Use of a vegetable oil other than (a) as component (e) increases the adhesiveness of the composition to plants and insect bodies, and allows the composition to be mixed more uniformly. In order to achieve this, it is desirable to use the vegetable oil in an amount not less than 1 part by mass, preferably, about 1-15 parts by mass.

The pesticidal/ovicidal composition of the present invention is preferably sprayed after dilution with water by preferably 100-fold to 1000-fold, more preferably 200-fold to 500-fold, so as to attain a total concentration of the active ingredients of preferably about 0.1 to 1% by mass, more preferably about 0.2 to 0.5% by mass.

It is preferable to spray, to crops, the pesticidal/ovicidal composition of the invention, in such an amount that the total amount of components (a), (b) and (c) is in the range between 0.2 kg/10a and 8 kg/10a, more preferably, in the range between 0.5 kg/10a and 3 kg/10a.

In general, the pesticidal/ovicidal composition of the invention can be applied from the initial phase to terminal phase of oviposition, however, the term for application depends on types of vermin pests. Although earlier application provides higher efficiency, the composition of the invention would work when applied even after laid eggs are identified due to its high ovicidal activity.

The pesticidal/ovicidal composition of the invention has a pesticidal effect on any agricultural vermin pests, and ovicidal effect on eggs thereof. Examples of the subject vermin pests include:

Lepidopteras: *Mamestra brassicae, Leucania separata* and *Plutella maculipennis*;
Tetranychidae: *Panonychus citri, Tetranychus urticae* and *Tetranychus kanzawai*;
Eriophyidae: *Aculus pelekassi* and *Aculops lycopersici*;
Tarsonemidae: *Brevipalpus obovatus*;
Astigmatae: *Tyrophagus similes*;
Aphidoideae: *Aphis gossypii, Myzus persicae* and *Aulacorthum solani*;
Hemipterae: *Trialeurodes vaporariorus* and *Bemisia tabaci*; and
Coccoideae: *Icerya purchasi, Unaspis yanonensis* and *Ceroplastes pseudoceriferus*.

EXAMPLES

The present invention will be explained more in detail by way of referring to Examples, Comparative Examples and Experimental Examples described below. However, these examples are not intended to limit the scope of the invention.

Adjuvant components (b) and (c) for pesticidal/ovicidal composition used in Examples and Comparative Examples below (hereinafter, an adjuvant containing both of these components will be referred to as "Adjuvant A") are in the form of a mixture of diglycerol monooleate (Adjuvant (c)) and polyoxyethylene (42 moles of oxyethylene added) castor oil (Adjuvant (b)) at a mass ratio of 3:1. Examples of diglycerol monooleate include Rikemal DO-100 (a product from Riken Vitamin Co., Ltd., Japan). Examples of polyoxyethylene (42 moles of oxyethylene added) castor oil include Solpole CA-42 (Toho Chemical Industry Co., Ltd., Japan).

Example 1

Sunflower oil (containing oleic acid in an amount of about 80% by mass) and Adjuvant A were mixed at a mass ratio (hereinafter, the same will be used) of 80:20 to produce Formulation 1.

Example 2

Safflower oil (containing oleic acid in an amount of about 80% by mass) and Adjuvant A were mixed at a ratio of 80:20 to produce Formulation 2.

Example 3

Extra virgin olive oil (containing oleic acid in an amount of about 80% by mass) and Adjuvant A were mixed at a ratio of 80:20 to produce Formulation 3.

Comparative Example 1

Comparative Formulation 1 contained Adjuvant A only.

Comparative Example 2

Cottonseed oil (containing oleic acid in an amount of about 30% by mass) and Adjuvant A were mixed at a ratio of 80:20 to produce Comparative Formulation 2.

Comparative Example 3

Castor oil (containing oleic acid in an amount of about 3% by mass) and Adjuvant A were mixed at a ratio of 80:20 to produce Comparative Formulation 3.

Comparative Example 4

Tung oil (containing oleic acid in an amount of about 9% by mass) and Adjuvant A were mixed at a ratio of 80:20 to produce Comparative Formulation 4.

Comparative Example 5

Grape seed oil (containing oleic acid in an amount of about 19% by mass) and Adjuvant A were mixed at a ratio of 80:20 to produce Comparative Formulation 5.

Comparative Example 6

Sunflower oil (Japanese local variety) (containing oleic acid in an amount of about 35% by mass) and Adjuvant A were mixed at a ratio of 80:20 to produce Comparative Formulation 6.

Comparative Example 7

Sunflower oil (medium level oleic acid variety) (containing oleic acid in an amount of about 45% by mass) and Adjuvant A were mixed at a ratio of 80:20 to produce Comparative Formulation 7.

Comparative Example 8

Safflower oil (Japanese local variety) (containing oleic acid in an amount of about 14% by mass) and Adjuvant A were mixed at a ratio of 80:20 to produce Comparative Formulation 8.

Experimental Example 1: Effect on *Tetranychus urticae* Koch eggs Formulations 1-3 and Comparative Formulations 1-8 were examined for their hatching inhibitory effects on eggs of *Tetranychus urticae* Koch. In brief, imagines of *Tetranychus urticae* Koch were released onto snap bean leaf discs and allowed to oviposit for three days while preventing drying by placing filter papers and a water-filled cup, followed by removal of the imagines to prepare *Tetranychus urticae* Koch eggs for experimental use. Each of the formulations diluted by 300-fold with water was sprayed to the leaf disc using a spray gun. Then, the leaf discs were incubated at 25° C. to culture the eggs. After five days, efficiency of hatching inhibition was estimated by counting the number of hatched larvae and unhatched eggs. The results are shown in FIG. 1.

Experimental Example 2: Pesticidal/Ovicidal Effect on *Tetranychus urticae* Koch Formulations 1 and 2 as well as Comparative Formulations 1-4 and 6-8 were examined for their pesticidal/ovicidal effects on *Tetranychus urticae* Koch. In brief, leaf discs for *Tetranychus urticae* Koch growth were cut out of snap bean leaves, on which *Tetranychus urticae* Koch had been preliminarily grown, and then left in a snap bean seedling pot for three days to allow *Tetranychus urticae* Koch to grow, followed by spraying each of the formulations diluted by 300-fold with water using a spray gun. Then, the snap bean pot was placed in a glass green house to grow *Tetranychus urticae* Koch. *Tetranychus urticae* Koch were observed daily and the preventive value was calculated based on the number of female imagines of *Tetranychus urticae* Koch 14 days after spraying.

Figure 2:
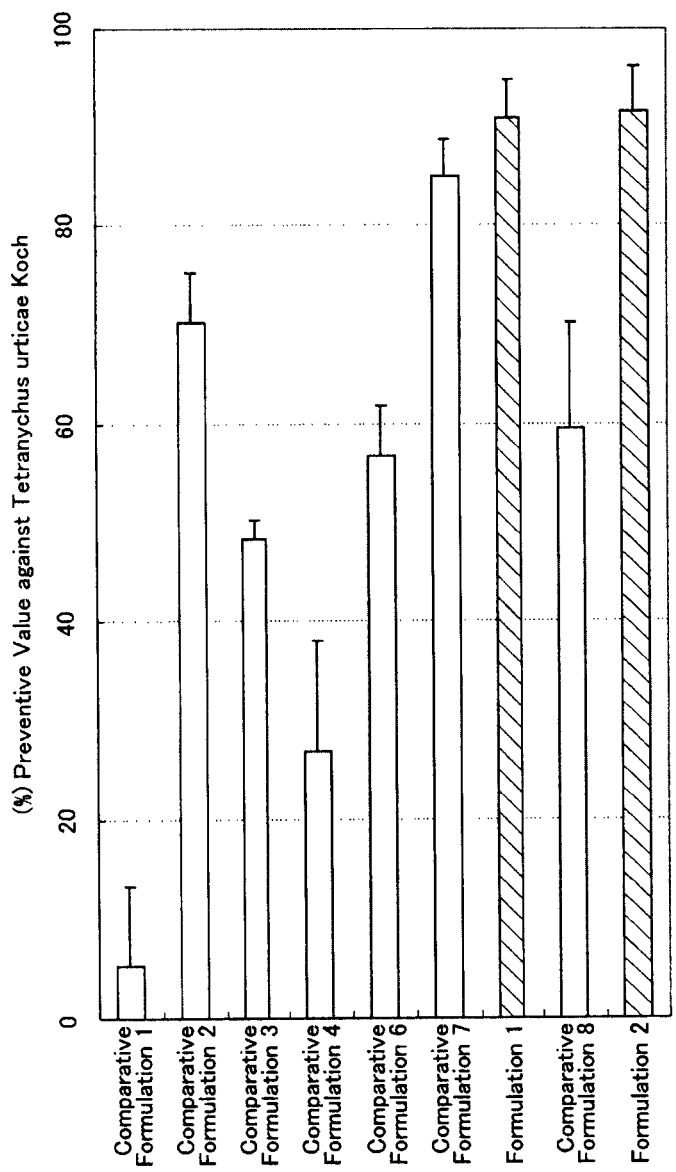
FIG. 2 sets forth the results of Experimental Example 2: Pesticidal/ovicidal effect on *Tetranychus urticae* Koch, wherein the percent of preventative value of Formulations 1-2 and Comparative Formulations 1-4 and 6-8 was examined.

(%) Preventive value=100−(%) corrected density index (%) corrected density index=$(A_1/A_0) \times (B_0/B_1) \times 100$ A₀: The number of female imagines of *Tetranychus urticae Koch* before treatment in treatment area
A₁: The number of female imagines of *Tetranychus urticae Koch* 14 days after treatment in treatment area
B₀: The number of female imagines of *Tetranychus urticae Koch* before treatment in non-treatment area
B₁: The number of female imagines of *Tetranychus urticae Koch* 14 days after treatment in non-treatment area The results are shown in FIG. 2.

Experimental Example 3: Pesticidal/Ovicidal Effect on *Tetranychus urticae Koch*

Formulations 4-11 used in Examples of the invention were prepared by mixing 85 parts by mass of safflower oil (containing about 80% by mass of oleic acid) and 15 parts by mass of component (b) listed in Table 3. Formulations 4-11 were examined for their pesticidal/ovicidal effects on *Tetranychus urticae Koch*. In brief, leaf discs for *Tetranychus urticae Koch* growth were cut out of snap bean leaves, on which *Tetranychus urticae Koch* had been preliminarily grown, and then left in a snap bean seedling pot for three days to allow *Tetranychus urticae Koch* to grow. Three days later, each of the formulations diluted with water (300 mg/100 ml) was sprayed using a spray gun. Then, the snap bean pot was placed in a glass green house to grow *Tetranychus urticae Koch*. *Tetranychus urticae Koch* were observed daily and the preventive value was calculated based on the number of female imagines of *Tetranychus urticae Koch* 14 days after spraying. The calculated numbers were categorized as follows. Non-treated areas were defined as reference. The pesticidal/ovicidal effect was evaluated according to the following criteria. The results are shown in Table 1.
A: 0-2 femail *Tetranychus urticae Koch* per leaf disc
B: 3-10 femail *Tetranychus urticae Koch* per leaf disc
C: 11-25 femail *Tetranychus urticae Koch* per leaf disc
D: 26 or more femail *Tetranychus urticae Koch* per leaf disc In this study, formulations were spayed to imagines and eggs. When the formulation used has no ovicidal effect, the eggs would hatch and eventually metamorphose to imagines. On the other hand, when the formulation has no pesticidal effect, the imagines would survive and lay eggs, which would hatch eventually. Therefore, the number of female imagines of *Tetranychus urticae Koch* can be employed as an index for the pesticidal/ovicidal effect of the formulation.

TABLE 1

| Formulation Nos. | Component (b) | Pesticidal/Ovicidal Effect |
|---|---|---|
| 4 | Sorbitan Monooleate (18-1) | B |
| 5 | Sorbitan Sesquioleate (18-1) | B |

TABLE 1-continued

| Formulation Nos. | Component (b) | Pesticidal/Ovicidal Effect |
|---|---|---|
| 6 | POE (20) Sorbitan Monooleate (18-1) | A |
| 7 | POE (8) Monooleate (18-1) | A |
| 8 | POE (8) Monostearate (18) | A |
| 9 | POE (30) Glyceryl Triisostearate | A |
| 10 | Disteareth-5 Lauroyl Glutamate | A |
| 11 | POE (40) hydrogenated castor oil PCA Isostearate | A |
| Untreated |  | D |

PCA: pyrrolidone carboxylic acid
Disteareth-5: POE (5) stearyl ether

Since the pesticidal/ovicidal composition according to the invention is prepared from food products and food additives as main materials, it has no stress on human bodies and natural environments and no risk of drug resistance induction, and can be applied to vermin pests which already have acquired resistances to other drugs. In addition, the composition according to the invention can be used at lower concentrations as compared to conventional methods. Furthermore, due to its excellent ovicidal effect, the composition can provide an increased preventive effect on a variety of crop pests per spray as compared to conventional pesticides.

What is claimed is:

1. A pesticidal/ovicidal method which comprises spraying a pesticidal/ovicidal composition onto a crop on which a crop pest is present to thereby cause pesticidal and/or ovicidal effect on the crop pest, wherein the pesticidal/ovicidal composition comprises, relative to 100 parts by mass of the total amount of components (a), (b) and (c),
    (a) 85 to 98.5 parts by mass of safflower oil containing 70 to 80% by mass of oleic acid as a fatty acid component;
    (b) 0.5 to 5 parts by mass of polyoxyethylene castor oil; and
    (c) 1.0 to 10 parts by mass of diglycerol oleate,
    (d) 0.1 to 3 parts by mass of 1-propanol, and
    (e) 1 to 15 parts by mass of cottonseed oil,
with the proviso that the total amount of components (a), (b) and (c) is 100 parts by mass,
wherein the crop pest is Tetranychidae.

2. The pesticidal/ovicidal method according to claim 1, wherein the pesticidal/ovicidal composition is sprayed onto the crop in such an amount that the total amount of components (a), (b) and (c) is in the range between 0.2 kg/10a and 8 kg/10a.

3. The pesticidal/ovicidal method according to claim 1, wherein the crop pest is *Tetranychus urticae*.

4. The pesticidal/ovicidal method according to claim 1, wherein the pesticidal/ovicidal composition is applied in a period from the initial phase to the terminal phase of oviposition.

* * * * *